(12) United States Patent
Ma et al.

(10) Patent No.: US 12,331,340 B1
(45) Date of Patent: Jun. 17, 2025

(54) EFFICIENT SYNTHESIS AND ASSEMBLY METHOD FOR LARGE FRAGMENT DNA BASED ON PROGRAMMABLE NUCLEASE ARGONAUTE

(71) Applicant: Hubei University, Wuhan (CN)

(72) Inventors: Lixin Ma, Wuhan (CN); Wanping Chen, Wuhan (CN); Jiakai Cui, Wuhan (CN); Miaomiao Chen, Wuhan (CN); Fei Wang, Wuhan (CN); Longyu Wang, Wuhan (CN); Xiaochen Xie, Wuhan (CN)

(73) Assignee: Hubei University, Wuhan (CN)

( * ) Notice: Subject to any disclaimer, the term of this patent is extended or adjusted under 35 U.S.C. 154(b) by 0 days.

(21) Appl. No.: 18/915,035

(22) Filed: Oct. 14, 2024

Related U.S. Application Data

(63) Continuation of application No. PCT/CN2024/095187, filed on May 24, 2024.

(30) Foreign Application Priority Data

Dec. 14, 2023 (CN) .......................... 202311725165.0

(51) Int. Cl.
| | |
|---|---|
| *C12P 19/34* | (2006.01) |
| *C12N 1/20* | (2006.01) |
| *C12N 9/22* | (2006.01) |
| *C12N 15/11* | (2006.01) |
| *C12N 15/70* | (2006.01) |
| *C12N 15/90* | (2006.01) |
| *C12R 1/19* | (2006.01) |

(52) U.S. Cl.
CPC .............. *C12P 19/34* (2013.01); *C12N 1/20* (2013.01); *C12N 9/22* (2013.01); *C12N 15/111* (2013.01); *C12N 15/70* (2013.01); *C12N 15/902* (2013.01); *C12N 2310/20* (2017.05); *C12R 2001/19* (2021.05)

(58) Field of Classification Search
None
See application file for complete search history.

(56) References Cited

U.S. PATENT DOCUMENTS 10,253,311 B2 * 4/2019 Doudna .................. C12P 19/34
2021/0087604 A1 * 3/2021 Zhao ........................ C12N 9/22

FOREIGN PATENT DOCUMENTS

| CN | 116606839 A | 8/2023 | |
|---|---|---|---|
| WO | WO-2015176339 A1 * | 11/2015 | ............. C12N 15/10 |

OTHER PUBLICATIONS

Enghiad B et al. Nat Commun. May 16, 2022;13(1):2697 (Year: 2022).*
Wang H et al. Nucleic Acids Res. Mar. 2014;42(5):e37 (Year: 2014).*
CNIPA (ISA), Written Opinion of the International Searching Authority (WO/ISA) for PCT/CN2024/095187, Sep. 9, 2024.

* cited by examiner

*Primary Examiner* — Kimberly Chong
*Assistant Examiner* — Douglas Charles Ryan
(74) *Attorney, Agent, or Firm* — Hemisphere Law, PLLC; Zhigang Ma

(57) ABSTRACT

An efficient synthesis and assembly method for the large fragment DNA based on the programmable nuclease Argonaute, specifically includes: constructing and treating antibiotic resistance gene reconstructed vectors with linearization, dividing a target DNA into multiple small DNA fragments and then synthesizing the small DNA fragments, followed by loading the synthesized small DNA fragments to the antibiotic resistance gene reconstructed vectors; and the SLIC and resistance gene reconstruction are used to achieve assembly of the target DNA. The method combines the SLIC with a resistance gene reconstruction strategy, allowing for the assembly of 5-6 small fragments in a single resistance gene reconstruction, which is more efficient and time-saving. Moreover, the number of the resistance gene reconstructions can be flexibly chosen according to the length of the DNA fragments. Mutations are not introduced caused by PCR, and the reconstructed large fragment do not need a second sequencing, saving time and costs.

9 Claims, 8 Drawing Sheets

Specification includes a Sequence Listing.

EFFICIENT SYNTHESIS AND ASSEMBLY METHOD FOR LARGE FRAGMENT DNA BASED ON PROGRAMMABLE NUCLEASE ARGONAUTE

CROSS-REFERENCE TO RELATED APPLICATIONS

This application is a continuation of International Patent Application No. PCT/CN2024/095187, filed on May 24, 2024, which claims the priority of Chinese Patent Application No. CN202311725165.0, filed on Dec. 14, 2023, both of which are herein incorporated by reference in their entirety.

TECHNICAL FIELD

The disclosure relates to the field of large fragment deoxyribonucleic acid (DNA) synthesis and assembly technologies, and more particularly to an efficient synthesis and assembly method for large fragment DNA based on a new type of programmable nuclease Argonaute (abbreviated as Ago).

STATEMENT REGARDING SEQUENCE LISTING

The sequence listing associated with this application is provided in text format in lieu of a paper copy and is hereby incorporated by reference into the specification. The name of the XML file containing the sequence listing is 24005JHG-USP1-ZL244915-USP1-SL-R.xml. The XML file is 17,609 bytes; is created on Feb. 18, 2025; and is being submitted electronically via patent center.

BACKGROUND

DNA synthesis plays an increasingly important role in various fields such as genetic engineering, clinical diagnosis and therapy, and forensic science etc. The DNA synthesis with large scale and low cost is expected to rapidly advance fields such as engineering biology, therapy, data storage, and nanotechnologies. In recent years, DNA synthesis technologies have made significant progress, but still face challenges in synthesis throughput, cost control, and especially in the synthesis of large fragment DNA. The assembly of the large fragment DNA still relies on cloning techniques that are time-consuming and expensive. The development of synthetic biology is currently facing a bottleneck in DNA supply, and the writing technology dominated by DNA synthesis has great room for improvement in terms of synthesis length, synthesis accuracy and synthesis cost. Currently, the assembly and transfer technology of small fragment DNA is relatively mature. A large molecular weight and susceptibility to breakage of the large fragment DNA makes an in vitro operation cumbersome and inefficient. Therefore, there is an urgent need to develop low-cost, high-efficiency DNA synthesis and large fragment DNA assembly methods to enhance the ability to "write DNA" and further expand the scope of DNA applications.

Currently, DNA assembly technologies mainly include three types: enzyme-dependent assembly, non-enzyme-dependent assembly, and in vivo homologous recombination-dependent assembly. The enzyme-dependent assembly includes an assembly method based on DNA polymerases, such as polymerase cycling assembly (PCA) based on polymerase chain reaction (PCR) technologies, which relies on high-fidelity proofreading PCR enzymes and is not suitable for the synthesis of long fragment DNA, and as a length of DNA increases, a mutation rate increases. The PCA is not applicable for the synthesis of special DNA sequences with high guanine and cytosine (GC) content and repetitive sequences. The enzyme-dependent assembly also include Bio-Brick and Golden Gate. However, the main limitations of the Bio-Brick and the Golden Gate are that element sequences cannot contain enzyme cutting site sequences in the prefix and suffix sequences, and the connection will form a scar sequence. The scar sequence may affect the function of a biological element and cannot achieve seamless assembly. Since the CRISPR-associated (Cas) protein needs a protospacer adjacent motif (PAM) sequence when playing a cutting role, a large fragment DNA assembly method based on the Cas programmable enzyme have scar effects and cannot achieve strict sense of seamless assembly. Moreover, the guide ribonucleic acid (RNA) of the Cas protein is a relatively long RNA, resulting in high assembly costs and low efficiency due to instability and high price of RNA.

In summary, the DNA synthesis, especially the assembly of the large fragment DNA, currently faces challenges such as low efficiency and high costs. Additionally, there is no efficient method for synthesizing special DNA sequences with high GC content and repetitive sequences, which greatly restricts the development and progress of synthetic biology. Therefore, there is an urgent need to develop efficient and low-cost DNA synthesis and large fragment DNA assembly technologies to promote the advancement of synthetic biology.

SUMMARY

In response to problems of the assembly of large fragment DNA in the related art, the disclosure provides an efficient synthesis and assembly method for large fragment DNA based on a programmable nuclease Argonaute.

The disclosure has the following technical solutions.

The efficient synthesis and assembly method for the large fragment DNA based on the programmable nuclease Argonaute specifically includes:

S1, constructing pNEW(Amp$^r$) plasmids as antibiotic resistance gene reconstructed vectors, where each pNEW(Amp$^r$) plasmid includes a filler fragment and resistance gene fragments, with m base pairs (bp) of a homologous sequence between the resistance gene fragments;

S2, excising the filler fragment from each pNEW(Amp$^r$) plasmid by using the programmable nuclease Argonaute and guide DNA (gDNA) to obtain linear vectors each with a 3' overhang of each linear vector of m nucleotides (nt);

S3, dividing a target DNA into n small DNA fragments with 450-500 bp, and synthesizing the small DNA fragments and introducing m nt of sequences which are complementary to homologous sequences of the linear vectors to the small DNA fragments to obtain synthesized small DNA fragments;

S4, mixing and transforming the linear vectors obtained from the step S2 and the synthesized small DNA fragments obtained from the step S3 in competent cells of *Escherichia coli* to obtain recombined plasmids pNEW(Amp$^r$) 1, 2, 3 to n; and S5, assembling the recombined plasmids pNEW(Amp$^r$) 1, 2, 3 to n based on the programmable nuclease Argonaute and resistance gene reconstruction.

In the disclosure, the programmable nuclease Argonaute is used to digest a plasmid into a linear vector, however, not all Argonautes or their mutants with the function of cutting double-stranded DNA (dsDNA) can achieve the efficient synthesis and assembly method for the large fragment DNA of the disclosure. It is found through experiments that the programmable nuclease Argonaute used in the disclosure has the activity to efficiently digest the dsDNA and plasmid DNA under magnesium ion ($Mg^{2+}$) conditions, especially when cutting the dsDNA with a GC content ≥50% (such as up to 70%), the programmable nuclease Argonaute can better achieve the method of the disclosure.

In an embodiment, a resistance gene in each pNEW (Amp$^r$) plasmid includes but is not limited to one or more selected from the group consisting of a Kanamycin resistance gene (Kan$^r$), a Chloramphenicol resistance gene (Chl$^r$), a Gentamicin resistance gene (Gen$^r$) and a Spectinomycin resistance gene (Spe$^r$). The number of the resistance gene can be set according to actual needs.

In an embodiment, the filler fragment of each pNEW (Amp$^r$) plasmid is ccdb lethal gene (with the sequence as shown in SEQ ID NO: 3). The ccdb lethal gene is used for counter-selection, resulting in a very low background, thereby reducing the workload for subsequent screening of recombinant colonies.

In a specific embodiment, the resistance gene of each pNEW(Amp$^r$) plasmid includes the Kan$^r$, the Chl$^r$, the Gen$^r$ and the Spe$^r$, the filler fragment of each pNEW(Amp$^r$) plasmid is the ccdb lethal gene, and there are 10 bp of each homologous sequence between the resistance gene fragments 5Kana/3Kana, 5Chl/3Chl, 5Gen/3Gen, and 5Spe/3Spe.

In an embodiment, the programmable nuclease Argonaute is APfAgo, with the amino acid sequence shown in SEQ ID NO: 1. Furthermore, the APfAgo is encoded by the gene sequence shown in SEQ ID NO: 2. The APfAgo is capable of cutting the dsDNA with a GC content of 70% by 80%-90% within 15 minutes (min).

In an embodiment, the step S2 specifically includes: designing the gDNA with 16-18 nt in response to the homologous sequences and performing 5' phosphorylation treatment on the gDNA with 16-18 nt to obtain 5'-P gDNA, incubating the 5'-P gDNA and the programmable nuclease Argonaute, and then mixing the 5'-P gDNA and the programmable nuclease Argonaute with the pNEW(Amp$^r$) plasmids for reaction, after the reaction, recovering the linear vectors each with the 3' overhang of m nt by using agarose gel electrophoresis for later use.

In a specific embodiment, the APfAgo is used to linearize a target plasmid, and reaction conditions are as follows: first, the 5'-P gDNA is incubated with the APfAgo at 70° C. for 5 min, then mixed with the target plasmid for reaction at 92° C. for 10 min.

In an embodiment, the synthesizing the small DNA fragments in the step S3 includes:
designing oligonucleotide primer pairs which are overlapping in a length of 17-20 nt and seamless in response to the small DNA fragments, and placing the oligonucleotide primer pairs and a LA Taq® buffer in a reaction tube for annealing followed by synthesizing the DNA fragments; where a length of each oligonucleotide primer is in a range of 50-59 nt, and 5' ends of the first and last oligonucleotide primers are introduced with the m nt of the sequences which are complementary to the homologous sequences of the linear vectors.

In an embodiment, procedures of the annealing include: 94° C. for 5 min, 94° C. to 37° C. slope 20 min, and 37° C. for 7 min.

In an embodiment, the step S5 specifically includes:
dividing the recombined plasmids pNEW(Amp$^r$) 1, 2, 3 to n into x groups with 2-6 recombined plasmids per group, taking and cutting the first and last recombined plasmids from each group with the programmable nuclease Argonaute to obtain fragments including target sequences and resistance gene units, cutting middle recombined plasmids from each group with the programmable nuclease Argonaute to obtain target fragments each with only a 3' overhang of m nt, mixing and transferring the fragments including the target sequences and the resistance gene units with the target fragments to competent cells of Escherichia coli without F plasmid (F$^-$) followed by screening to obtain x recombinants (i.e., new recombined plasmids), and repeating above steps until the small DNA fragments are assembled to the target DNA. Since the resistance gene recombination is used for positive genetic selection, there is no contamination from uncut background plasmids. The digest products (i.e., the fragments including the target sequences and the resistance gene units and the target fragments) do not need to be recovered.

It should be noted that, in the step S5, a method for selecting the recombinants can be achieved not only by spreading on plates but also by culturing in liquid medium supplemented with antibiotics with corresponding resistance genes, which further shortens the cycle time and reduces costs.

In the disclosure, starting from small DNA fragments of 450-500 bp, if 6 fragments are assembled at one time and a resistance gene is reconstructed, a fragment of 3 kilobases (kb) in length can be obtained, which can meet more than 99% of gene synthesis. Reconstructing twice can assemble up to 18 kb, thereby meeting the synthesis of more than 99% of large fragment DNA. Reconstructing three times can reach 30 kb.

Compared to the related art, the disclosure has the following beneficial effects.

(1) The disclosure divides the large fragment DNA into small fragment units of 450-500 bp for re-synthesis. The small fragment units are directly annealed through seamless oligonucleotide primer pairs. The complementary base pairing of hydrogen bonds is utilized, and the small fragment units are annealed with vectors having sticky ends to form nicked circular plasmids. The nicked circular plasmids are transformed in the Escherichia coli and synthesized by utilizing the repair system of the Escherichia coli. Since there is no introduction of a PCR amplification step, mutations caused by PCR amplification are not introduced, which greatly increases the synthesis accuracy.

(2) In the disclosure, the ccdb lethal gene is introduced into the antibiotic resistance genes reconstructed vectors. By utilizing the principle of the ccdb lethality, the transformation is carried out using the competent cells of the Escherichia coli without the F plasmid (F$^-$). This allows background plasmids that do not have the target fragment inserted to be lethal and unable to grow due to the ccdb lethal gene, significantly reducing the background and improving the efficiency of transformation and recombination, as well as reducing the workload for screening recombinants.

(3) The disclosure combines the use of sequence and ligation independent cloning (SLIC) and resistance gene reconstruction strategies to assemble the small DNA fragments. By using the programmable nuclease Argonaute for enzyme cutting to obtain small DNA units, PCR operation is not required. The products after enzyme cutting are directly transformed in the *Escherichia coli*. Genetic selection is performed using reconstructed resistance genes, which avoids mutations caused by PCR amplification. Therefore, the mutation rate is extremely low, or even zero, eliminating the need for secondary sequencing, thereby reducing costs. Combined with the SLIC, multiple fragments can be assembled in one reconstruction, increasing efficiency and shortening the synthesis cycle. One reconstruction takes only one day, which means that starting from a 450-500 bp target fragment plasmid sequenced to be correct, it is possible to assemble up to 30 kb in 3 days.

(4) The operation system of the disclosure is simple, only the programmable nuclease Argonaute (Ago) is used for cutting plasmids. The enzyme cutting products can be directly transformed into the *Escherichia coli*, without the need of purification and ligation.

(5) The disclosure utilizes the principle of resistance gene reconstruction, assembling multiple target fragments with complementary homologous sequences during the resistance gene reconstruction. Positive genetic selection is performed with the corresponding antibiotic of the reconstructed resistance. After the addition of the corresponding antibiotic, only those who have reconstructed a complete corresponding resistance gene can grow. Uncut plasmids or incorrectly reconstructed products that fail to obtain a complete resistance gene cannot grow on an antibiotic-containing medium, resulting in high accuracy and simple operation.

(6) Special DNA sequences can be synthesized, such as highly repetitive sequences, Poly A, and other Poly sequences, which can be used to study complex structures or regulatory DNA sequences. Since the efficient synthesis and assembly method for the large fragment DNA starts with plasmids and obtains fragments through enzyme cutting without the need for PCR, highly repetitive sequences that PCR methods cannot produce can be synthesized.

(7) Due to the use of antibiotic resistance genes for the positive selection, there is no fear of interference from the background plasmids. The transformants of the reconstructed recombined plasmids can be cultured directly in liquid medium with the corresponding antibiotic of the reconstructed resistance genes without the need for plate spreading operations. This means that the selection operation is simple and can be performed in solution, which is conducive to automation and further shortens the cycle.

(8) It is beneficial for constructing mutant libraries, and the efficiency for site-directed mutagenesis and directed evolution is very high. The screening workload can be reduced by 2-3 orders of magnitude compared to methods for constructing mutant libraries in the related art.

DETAILED DESCRIPTION OF EMBODIMENTS

Figure 1:
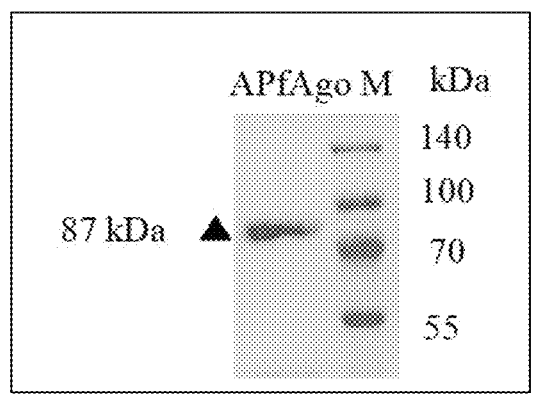
FIG. 1 illustrates a sodium dodecyl sulfate-polyacrylamide gel electrophoresis (SDS-PAGE) identification analysis result diagram of a programmable nuclease Argonaute (APfAgo) according to an embodiment of the disclosure.

The technical solutions of the disclosure are clearly and completely described below in conjunction with embodiments and accompanying drawings. It should be understood that the specific embodiments described herein are only for illustrating and explaining the disclosure, and are not intended to limit the disclosure.

Unless otherwise defined, all technical and scientific terms used in this article have the same meanings as those commonly understood by those skilled in the art. The terms "including" and "having" and any variations thereof in the specification and claims of the disclosure are intended to cover non-exclusive inclusion.

In order to solve the problems of low efficiency, high cost, high GC content, and difficulty in synthesizing special DNA such as repetitive sequences in large fragment DNA assembly technologies in the related art, the disclosure provides a method for synthesizing and assembling large fragment DNA based on a programmable nuclease Argonaute.

The method includes the following steps (1)-(5).

(1) Preparation of an Antibiotic Resistance Gene Reconstructed Vector Used to Assemble DNA Fragments.

The antibiotic resistance gene reconstructed vector for assembling DNA fragments described in the disclosure includes a filler fragment and resistance gene fragments, with homologous sequences for SLIC between the resistance gene fragments.

In a specific embodiment of the disclosure, a plasmid pET-23a is selected as a starting vector for modification. $Kan^r$, $Chl^r$, $Gen^r$, and $Spe^r$ genes are amplified using respective plasmids as templates. Ultimately, a pNEW($Amp^r$) plasmid is constructed. The pNEW($Amp^r$) plasmid uses a ccdb lethal gene as the filler fragment, and a length of each homologous sequence is 10 bp.

(2) Preparation of Linear Vectors.

The antibiotic resistance gene reconstructed vector, which has been sequenced and confirmed to be correct, is cut with Ago enzyme (i.e., the programmable nuclease Argonaute). Suitable gDNAs are designed to cut out the filler fragment (ccdb lethal gene), to obtain each linear vector with a 3' overhang of 10 nt. Cut products (the linear vectors) are performed with gel recovery and then stored at −20° C. for later use.

(3) Synthesis of Small DNA Fragments.

A target DNA is selected and divided into small fragment units, and then, each small DNA fragment is synthesized separately.

For example, for small DNA fragments that are 450-500 bp in length, oligonucleotide primer pairs which are seamless and overlapping with 17-20 nt in length are designed. 16 oligonucleotide primers with a length of 50-59 nt are synthesized for each 450-500 bp fragment. 5' ends of the first and last oligonucleotide primers are separately introduced with sequences that are complementary to homologous sequences of the linear vectors. Then, the 16 oligonucleotide sequences are diluted to a final concentration of 10 moles per liter (M) to obtain diluted oligonucleotide sequences. 0.5 microliters (μL) of each oligonucleotide sequence are taken and then added into a PCR tube. Then, 2 μL of 10× Buffer [500 millimoles per liter (mM) potassium acetate (KAc), 200 mM Tris(hydroxymethyl)aminomethane acetate (Tris-Ac), 100 mM magnesium acetate (MgAc), 1 milligram per milliliter (mg/mL) bovine serum albumin (BSA)] is added to each PCR tube followed by adding double-distilled water ($ddH_2O$) to each PCR tube to a final volume of 20 μL and mixing well. Finally, each PCR tube is annealed by gradual cooling procedures of: 94° C. for 5 min, a temperature gradient from 94° C. to 37° C. during 20 min (i.e., 94° C.-37° C. slope 20 min), and 37° C. for 7 min to obtain the small DNA fragments.

(4) Preparation of Recombined Plasmids by SLIC.

The linear vectors are mixed with the small DNA fragments and then directly transformed into competent cells of *Escherichia Coli* (such as DH5a) which lack an F factor to obtain transformed cells. The transformed cells are coated on ampicillin resistance plates followed by recombinant screening and sequencing to obtain recombined plasmids which are sequenced to be correct, respectively named as pNEW($Amp^r$) 1, pNEW($Amp^r$) 2, pNEW($Amp^r$) 3, and so on.

(5) Assembly of Large Fragment DNA Based on the SLIC and Resistance Gene Reconstruction Strategy.

While reconstructing the resistance genes, multiple target fragments with complementary homologous sequences are assembled together via the SLIC.

A 30 kb DNA fragment is taken as an example and divided into 60 fragments with about 500 bp per fragment. Following the above steps, 60 first recombed plasmids are obtained by using the pNEW($Amp^r$) plasmid. The 60 first recombined plasmids are divided into 10 groups, with 6 first recombined plasmids per group, for a first reconstruction, so as to obtain second recombined plasmids by the first reconstruction. Specifically, for each group: the first recombined plasmids including the first and last fragments are cut with the Ago enzyme to obtain fragments including target sequences and resistance gene units; the first recombined plasmids including the middle fragments are cut with the Ago enzyme to obtain target fragments with only a 3' overhang of homologous sequences per target fragment. The cut products (i.e., the fragments including target sequences and resistance gene units and the target fragments) from each group are mixed and directly transformed into the *Escherichia coli* and then coated on $Kan^r$ resistance agar plates, followed by screening to obtain 10 second recombined plasmids (one from each group), with a target DNA fragment size of each second recombined plasmid of approximately 3 kb.

The 10 second recombined plasmids obtained from the first reconstruction are divided into 2 groups, with 5 second recombined plasmids per group. Following steps of the first reconstruction, a second reconstruction is performed with the resistance gene $Chl^r$ to obtain 2 third recombined plasmids, a target DNA fragment size of each third recombined plasmid is about 15 kb. The 2 third recombined plasmids obtained from the second reconstruction are cut and a third reconstruction is performed with the resistance gene $Gen^r$ to obtain a plasmid including the 30 kb DNA fragment.

The method of the disclosure starts with a plasmid and does not involve PCR, thus avoiding mutations caused by the PCR. The assembled large fragment does not require secondary sequencing, which reduces costs. Moreover, the method uses the antibiotic resistance gene reconstruction for positive genetic selection. By taking advantage of the difference in resistance between the recombined plasmids and the starting plasmid, products after transformation are recombinants. This simplifies the operation steps and reduces costs, making it easier to achieve automated operations. Additionally, the enzyme cutting system only requires a single Ago enzyme, which simplifies the system. By utilizing the different resistances of the recombinants and the background plasmids for selection, there is no interference from the background plasmids. The cut fragments do not need to be recovered and purified, and there is no need for enzyme ligation operations. Direct transformation is possible without the need for special expensive equipment such as a PCR machine, making the operation simple.

In the method of the disclosure, the Ago enzyme or its mutant can achieve the disclosure as long as the following conditions are met.

The Ago enzyme or its mutant possesses the activity to efficiently cleave dsDNA and plasmid DNA under $Mg^{2+}$ conditions, and to cleave dsDNA with high GC content (such as 70%).

Compared to a programmable nuclease Cas, the programmable nuclease Argonaute does not require a PAM recognition sequence when cleaving DNA, and the cleavage is not restricted by any sequence. Only a single 16-18 nt gDNA is required to cleave at any site, which facilitates seamless assembly. There is no need to avoid any cleavage sites, offering advantages of simple experimental design and easy operation.

The following are some specific embodiments. It should be noted that the embodiments described below are exemplary and are only used to explain the disclosure, and should not be understood as limiting the disclosure. If specific technology or conditions are not specified in the embodiments, they shall be carried out according to the technology or conditions described in the literature in the art or as per the product instructions. Reagents or instruments without specified manufacturers are all conventional products that can be obtained through regular purchase channels.

Embodiment 1

Taking synthesis of a 30 kb DNA fragment as an example, the synthesis and assembly of large fragment DNA is achieved in the embodiment through the following steps (1)-(6).

(1) Expression and Purification of Argonaute.

The programmable nuclease Argonaute used in the embodiment is a *Pyrococcus furiosus* Argonaute (PfAgo) mutant (referred to as APfAgo), with the amino acid sequence as shown in SEQ ID NO: 1. A preparation method of the APfAgo is as follows.

The APfAgo gene sequence (as shown in SEQ ID NO: 2) is ligated to pET28a to obtain a pET28a-APfAgo plasmid, and the pET28a-APfAgo plasmid is transformed into *Escherichia coli* BL21(DE3) to obtain transformed cells. A single colony of the transformed cells is inoculated into a Luria-Bertani (LB) liquid medium containing 50 micrograms per milliliter (μg/mL) kanamycin and then the LB liquid medium is placed in a shaking incubator for culturing at 37° C. and 220 revolutions per minute (rpm). When the optical density at 600 nanometers ($OD_{600}$) of the bacterial culture reaches 0.8, the LB liquid medium is transferred to a shaking incubator at 18° C. for induction with isopropyl-beta-D-thiogalactopyranoside (IPTG) overnight, followed by centrifuging at 6000 rpm for 10 min to obtain bacterial cells, the bacterial cells are washed with Buffer A {20 mM 2-[4-(2-hydroxyethyl)piperazin-1-yl]ethanesulfonic acid (HEPES) buffer with pH of 7.5, 250 mM sodium chloride (NaCl), 1 mM dithiothreitol (DTT)}, and then resuspended in the Buffer A with a final concentration of 1 mM phenyl methane sulfonyl fluoride (PMSF) added followed by disrupting cells at high pressure to obtain disrupted cells, and the disrupted cells are centrifuged at 18000 rpm for 30 min to obtain a supernatant.

The supernatant is filtered and then purified by nickel-nitrilotriacetic acid (Ni-NTA) purification followed by washing with 20 mM and 50 mM imidazole each for 10 column volumes (added in 3 times separately) to obtain a first washed product, the first washed product is washed with 100 mM imidazole, 200 mM imidazole, and 300 mM imidazole each for 3 column volumes to obtain a second washed product, and samples are taken from the second washed product for SDS-PAGE analysis. Then, elution fractions containing highly purified target protein are collected and then ultrafiltration to buffer exchange to the Buffer A are performed on the elution fractions to obtain an intermediate product. A NaCl concentration of the intermediate product is diluted to 125 mM with 20 mM HEPES (pH 7.5), and then the intermediate product is purified by heparin column purification using heparin column (HiTrap™ Heparin HP, GE Healthcare) to obtain a purified protein; where the heparin column is equilibrated in advance with Buffer B (20 mM HEPES pH 7.5, 125 mM NaCl), and the APfAgo is eluted by increasing the concentration of NaCl. After confirming purity of the purified protein with SDS-PAGE and validating activity of the purified protein, the purified protein is aliquoted and then quickly frozen in liquid nitrogen, and stored at −80° C.

The purified protein is concentrated using a MILLIPORE 50-kDa ultrafiltration tube at 4° C. and 4000 rpm, followed by buffer exchange to remove imidazole to obtain an imidazole-removed product. An enzyme concentration of the imidazole-removed product is quantitatively determined using a bicinchoninic acid (BCA) assay kit, following operating instructions. BSA is used as a standard to prepare a standard solution and plot a standard curve, thereby calculating a concentration of the purified APfAgo.

The SDS-PAGE identification analysis result is shown as FIG. 1, an expected size of the APfAgo is 87 kilodaltons (kDa), calculated through Expasy (Swiss Bioinformatics Resource Portal).

(2) Preparation of an Antibiotic Resistance Gene Reconstructed Vector.

In this embodiment, a plasmid pET-23a is selected as a starting vector and modified to construct a pNEW(Amp$^r$) plasmid as the antibiotic resistance gene reconstructed vector. The specific steps are as follows.

Four plasmids pET-28a, pASK-IBA7C, pDONR223, and pMP2463 with different antibiotic resistances are used as templates, followed by PCR amplification to obtain resistance genes Kan$^r$, Chl$^r$, Gen$^r$, and Spe$^r$, respectively. Based on this, several rounds of overlap extension PCR are conducted to fuse all fragments into four target fragments, the four target fragments are purified through gel recovery and then cloned in equal molar ratios of 1:1:1:1 mediated by T5 exonuclease. Then, positive clones are preliminarily screened by colony PCR and sent to a biotech company for sequencing. A plasmid named pNEW(Amp$^r$) is extracted from colonies which are sequenced to be correct, and stored at −20° C. for later use.

In the pNEW(Ampr) plasmid, there are 10 bp of homologous sequences between each resistance gene fragment: 5Kana/3Kana, 5Chl/3Chl, 5Gen/3Gen, and 5Spe/3Spe, which are used for subsequent gDNA design.

Figure 2:
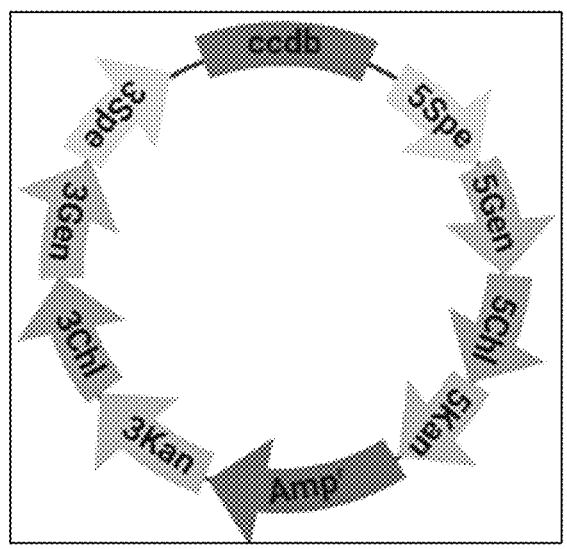
FIG. 2 illustrates a schematic structural diagram of an antibiotic resistance gene reconstructed vector pNEW (Amp$^r$) plasmid according to the embodiment of the disclosure.

FIG. 2 illustrates a schematic structural diagram of the pNEW(Amp$^r$) plasmid. A ccdb lethal gene is as a filler fragment, used for subsequent small DNA fragment cloning.

(3) Verification of the Cutting Activity of the APfAgo on the pNEW(Amp$^r$) Plasmid and Linearization Treatment.

Since the APfAgo targeted cuts single-stranded DNA (ssDNA) through gDNA, in the embodiment, two pairs of 16 nt gDNA are designed to cut dsDNA (i.e., the pNEW(Amp$^r$) plasmid), and the gDNA is treated with 5' phosphorylation to obtain 5'-P-gDNA.

A cutting and detection process is as follows. First, the 5'-P-gDNA is incubated with the APfAgo at 70° C. for 5 min, and then mixed with the pNEW(Amp$^r$) plasmid for reactions at 92° C. for 1 min, 3 min, and 5 min, respectively to obtain a reacted mixture. The reacted mixture is added with 2 μL of 6×DNA loading, and is detected by 1.0% agarose gel electrophoresis. Incubation and reaction systems used in this process are shown in Tables 1 and 2, respectively.

Figure 3:
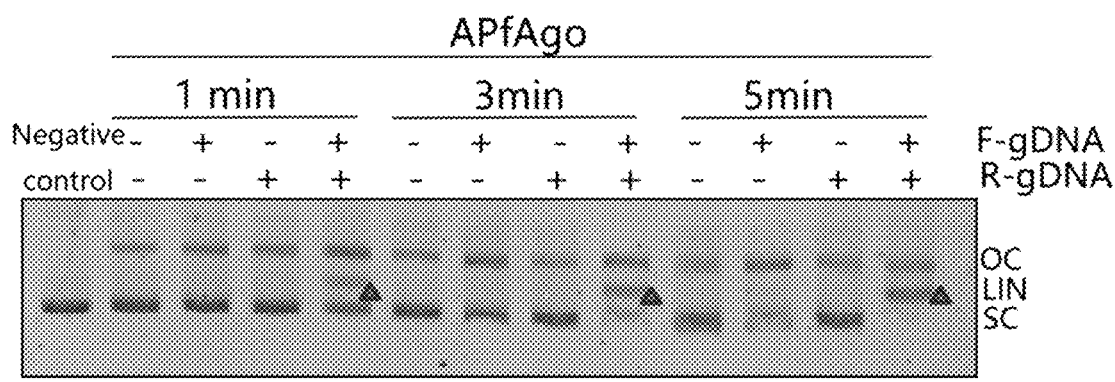
FIG. 3 illustrates an agarose gel electrophoresis detection result diagram of products obtained from the pNEW(Amp$^r$) plasmid under different cutting time of the APfAgo in the embodiment of the disclosure; where OC represents an open circular plasmid (one strand of a plasmid is broken), LIN represents a linearized plasmid (both strands of a plasmid are broken), and SC represents a supercoiled plasmid, and a triangle represents an enzyme cutting product.

Detection results are shown in FIG. 3: the APfAgo can use a pair of 5'-P-gDNA to target one strand of the pNEW (Amp$^r$) plasmid separately, cut the pNEW(Amp$^r$) plasmid which is supercoiled and generate linearized plasmid DNA. Moreover, as the cutting time increases, a content of linearized plasmid in the product increases.

TABLE 1 the incubation system of gDNA and APfAgo

| Components | Volume |
| --- | --- |
| APfAgo (2 mg/mL) | 0.2 μL |
| MgSO$_4$ (100 mM) | 0.6 μL |
| 10 × APfAgo reaction buffer | 2 μL |
| gDNA (10 micromoles per liter, μM) | 4 μL |
| ddH$_2$O | added up to 10 μL |

TABLE 2 the reaction system of cutting plasmid by the APfAgo

| Components | Volume |
| --- | --- |
| gDNA incubation system | 6.8 μL |
| plasmid | 2 μg |
| ddH$_2$O | added up to 20 μL |

Referring to above enzyme cutting conditions, the pNEW (Amp$^r$) plasmid is cut by the APfAgo for 10 min to obtain linear vectors, with a 3' overhang of 10 nt of each linear vector. The linear vectors are recovered by agarose gel and stored at −20° C. for later use.

(4) The Cutting Activity of the APfAgo on Regions with Different GC Contents.

Figure 4:
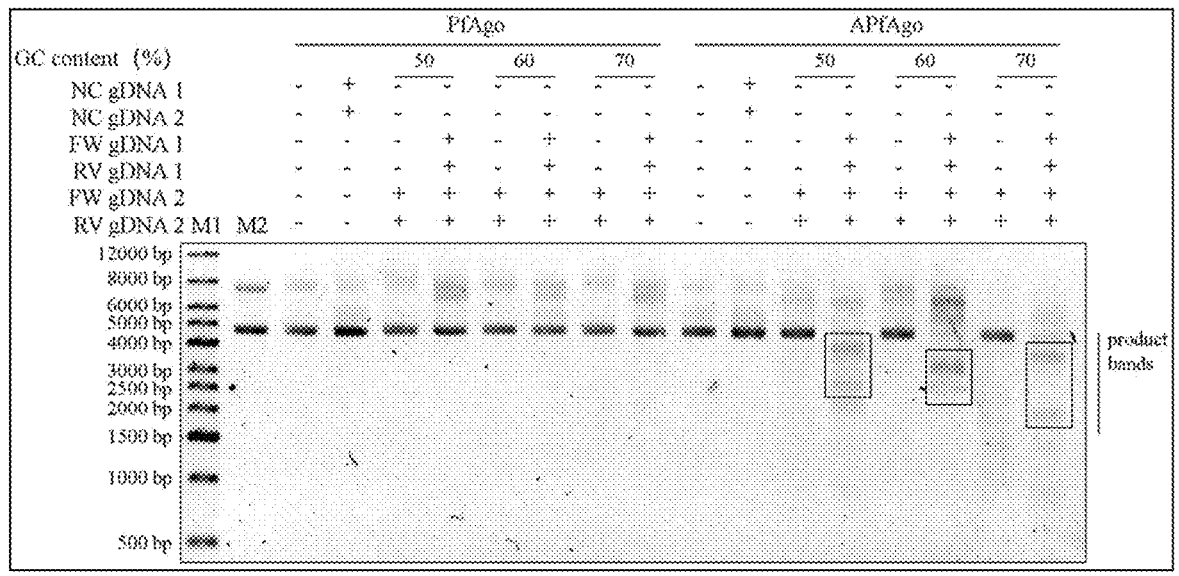
FIG. 4 illustrates an agarose gel electrophoresis detection result diagram of products obtained from cutting dsDNA with different GC contents by the APfAgo according to the embodiment of the disclosure, where product bands represent cutting products.

In order to investigate the cutting activity of the APfAgo on high GC content regions of plasmids, three sets of gDNA with different GC contents (50%, 60%, and 70%) are designed for the pNEW(Amp$^r$) plasmid. First, target bands are amplified by PCR to obtain linear dsDNA, and the linear dsDNA is subjected to cutting experiments to obtain cutting products. The cutting products are detected by 1.0% agarose gel electrophoresis to test the enzyme cutting results. The experimental results prove that the APfAgo can cut on regions with up to 70% GC content, while a wild-type PfAgo has no cutting activity on dsDNA with a GC content of 50% or higher, as shown in FIG. 4.

(5) Synthesis of Small Fragment pNEW(Ampr) Plasmids.

A target DNA is divided into n fragments with 500 bp per fragment and synthesized through the following process. Oligonucleotide primer pairs which are seamless and overlapping with 17-20 nt are designed. Each 500 bp fragment requires the synthesis of 16 oligonucleotide primers, approximately 50-59 nt in length per oligonucleotide primer, with 5' ends of the first and last oligonucleotide primers introduced with 10 nt sequences that are complementary to homologous sequences of the linear vectors. Then, the 16 oligonucleotide sequences are diluted to a final concentration of 10 M, 0.5 μL of each oligonucleotide sequence is taken and added into a PCR tube separately, 2 μL of 10× Buffer (500 mM KAc, 200 mM Tris-Ac, 100 mM MgAc, 1 mg/mL BSA) is added to each PCR tube, and then ddH$_2$O is added to each PCR tube to a final volume of 20 μL followed by mixing; finally, each PCR tube is annealed according to gradual cooling procedures of 94° C. for 5 min, 94° C. to 37° C. slope during 20 min, and 37° C. for 7 min to obtain small DNA fragments.

Figure 5:
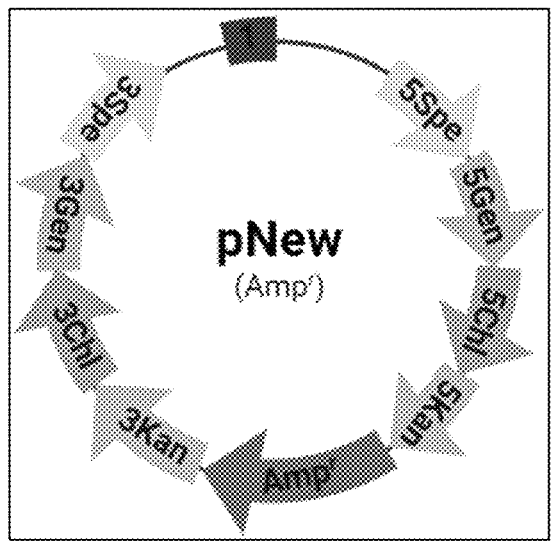
FIG. 5 illustrates a schematic structural diagram of a recombined plasmid formed by introducing small fragment DNA according to the embodiment of the disclosure.

The linear vectors obtained in the step (3) are mixed with the small DNA fragments and placed at 37° C. for 30 min, and then directly transformed into competent cells of *Escherichia Coli* DH5a which lack an F factor to obtain transformed cells. The transformed cells are coated on ampicillin resistance plates. All that grow are recombinants, due to background plasmids containing the ccdb lethal gene. Recombined plasmids which are sequenced to be correct, are named as pNEW(Amp$^r$) 1, 2, 3 to n. The structure of each recombined plasmid is shown in FIG. 5.

(6) Assembly of Large Fragment DNA.

The disclosure utilizes a resistance gene reconstruction strategy for assembly, where 2-6 plasmids can be reconstructed at each time. The following exemplarily illustrates the specific operation.

1. Taking synthesis of an 8 kb DNA fragment as an example, 16 recombined plasmids are prepared from the target DNA according to the step (5), and are divided into 8 groups, with 2 plasmids per group.

Figure 6:
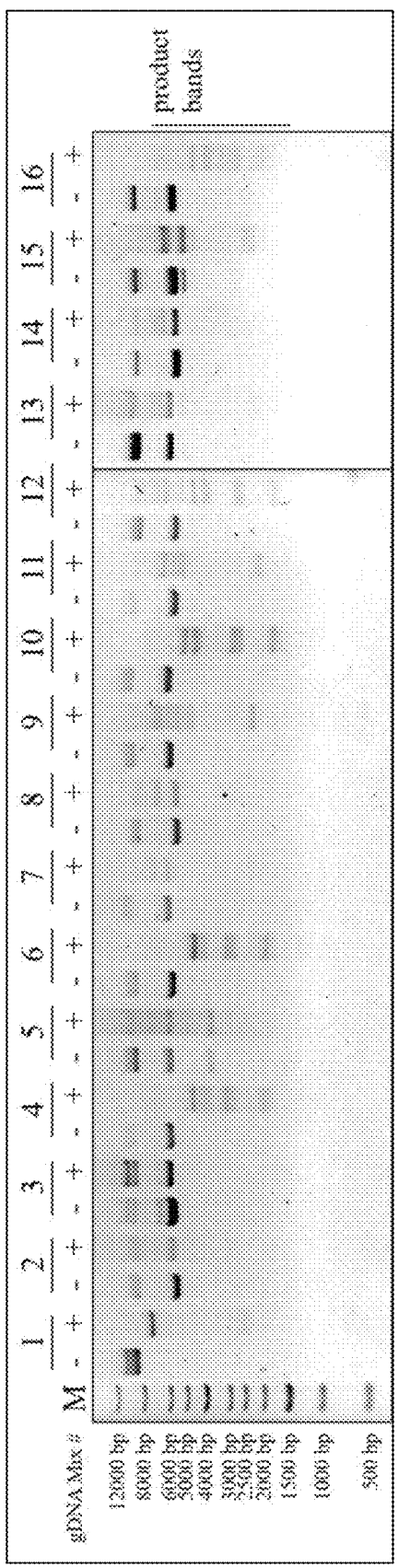
FIG. 6 illustrates an agarose gel electrophoresis detection result diagram of enzyme cutting of 1-16 plasmids in a first reconstruction according to the embodiment of the disclosure.
Figure 7:
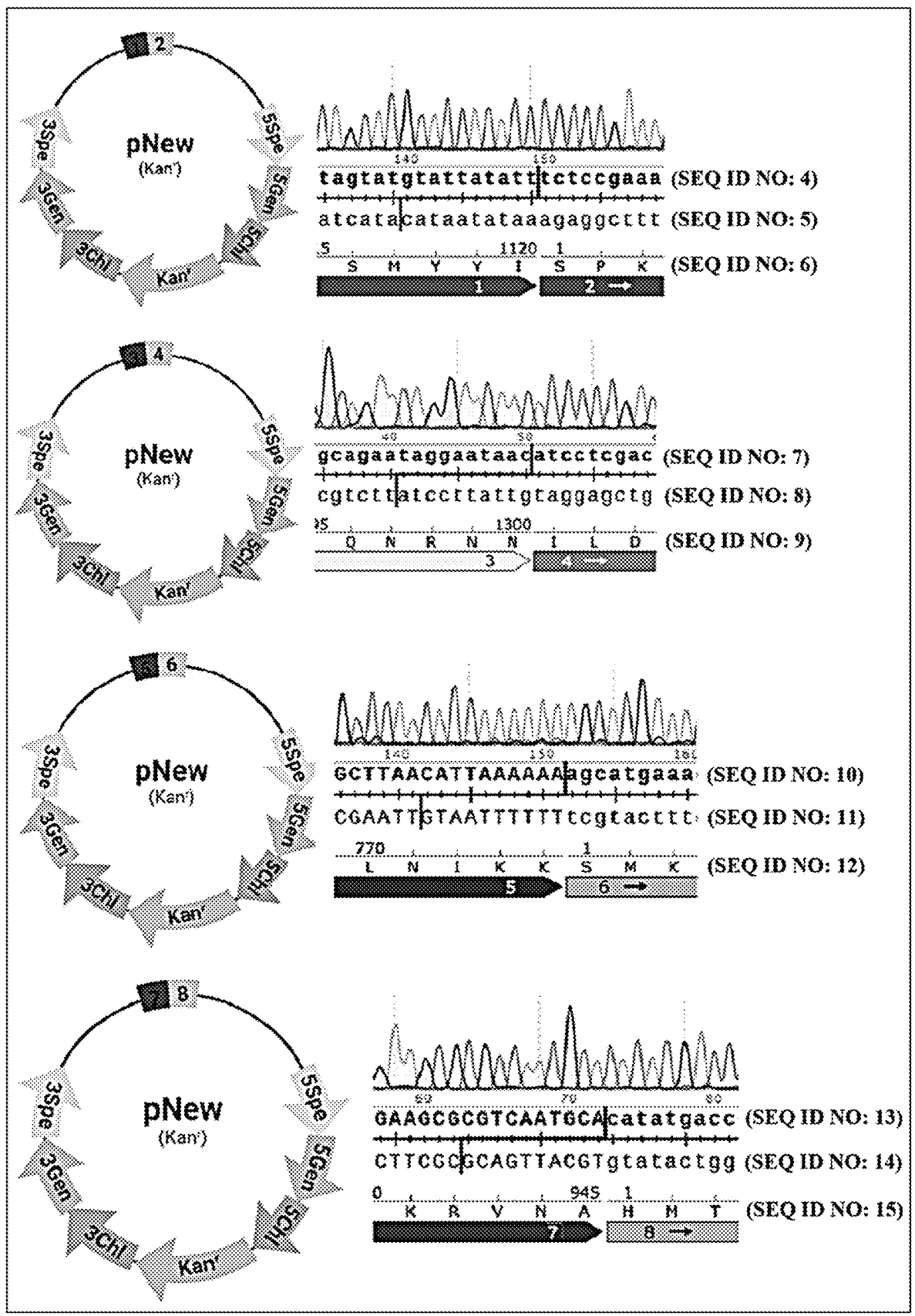
FIG. 7 illustrates a peak diagram of a sequencing result at a junction of the recombined plasmid after the first reconstruction of Kan$^r$ resistance according to the embodiment of the disclosure, which includes the nucleotide and amino acid sequences as shown in SEQ ID NO: 4 to SEQ ID NO: 15.
Figure 8:
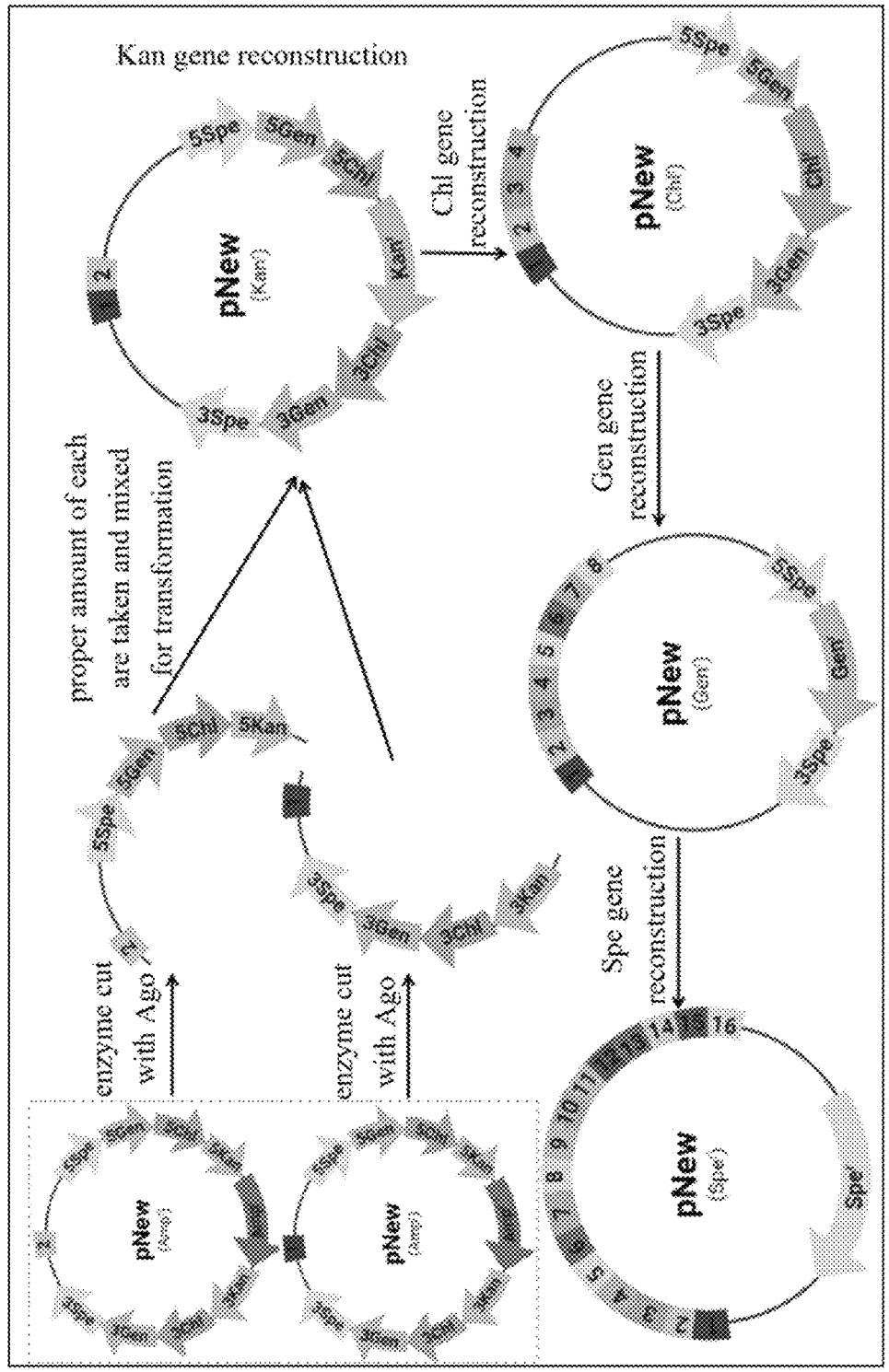
FIG. 8 illustrates a flowchart for assembling large fragment DNA based on a strategy of Argonaute, SLIC, and antibiotic resistance gene reconstruction (assembling and reconstructing 2 plasmids at a time) according to the embodiment of the disclosure.

Kan$^r$ resistance reconstruction is first performed, the 8 groups of recombined plasmids pNEW(Amp$^r$) are cut with their corresponding gDNA for 10 min (conditions are the same as in the step (3)) respectively to obtain enzyme cutting products, and the enzyme cutting products are tested by 0.7% agarose gel electrophoresis, as shown in FIG. 6. 2 μL of each enzyme cutting product is taken and mixed and then directly transformed into *Escherichia Coli* to obtain transformed cells, the transformed cells are directly cultured with an LB liquid medium containing 50 g/mL kanamycin, followed by extracting 8 plasmids (i.e., first reconstructed plasmids: pNEW(Kan$^r$) 1-2, pNEW(Kan$^r$) 3-4, pNEW (Kan$^r$) 5-6, pNEW(Kan$^r$) 7-8, pNEW(Kan$^r$) 9-10, pNEW (Kan$^r$) 11-12, pNEW(Kan$^r$) 13-14, pNEW(Kan$^r$) 15-16, where 1-16 respectively represent different small fragment DNA). The 8 plasmids are sent to a company for sequencing. Sequencing results (shown in FIG. 7) indicate that there are no additions or deletions of bases at cutting sites, and no scars are produced at connection points. The 8 plasmids pNEW(Kan$^r$) are divided into 4 groups with 2 plasmids pNEW(Kan$^r$) per group and then Chl$^r$ resistance reconstruction is performed on the 4 groups to obtain 4 plasmids pNEW(Chl$^r$) (i.e., second reconstructed plasmids: pNEW (Chl$^r$) 1-4, pNEW(Chl$^r$) 5-8, pNEW(Chl$^r$) 9-12, pNEW (Chl$^r$) 13-16). The 4 plasmids pNEW(Chl$^r$) are divided into 2 groups with 2 plasmids pNEW(Chl$^r$) per group and then Gen$^r$ resistance reconstruction is performed on the 2 groups to obtain 2 plasmids pNEW(Gen$^r$) (i.e., third reconstructed plasmids: pNEW(Gen$^r$) 1-8 and pNEW(Gen$^r$) 9-16). Spe$^r$ resistance reconstruction is performed on the 2 plasmids pNEW(Gen$^r$) to obtain a plasmid pNEW(Spe$^r$) containing a target DNA fragment, so as to finish DNA assembly. An assembly process is shown as FIG. 8.

2. 60 recombined plasmids are prepared from the target DNA according to the step (5), and are divided into 10 groups, with 6 plasmids per group. In each group, the recombined plasmids pNEW(Amp$^r$) including first and last fragments (taking the first group as example, pNEW(Amp$^r$) 1 and pNEW(Amp$^r$) 6) are cut by the APfAgo for 10 min (conditions are the same as in the step (3)) respectively to obtain fragments including target sequences and resistance gene units. The recombined plasmids including the middle fragments (taking the first group as example, pNEW(Amp$^r$) 2, pNEW(Amp$^r$) 3, pNEW(Amp$^r$) 4, and pNEW(Amp$^r$) 5) are cut with the APfAgo to obtain target fragments with only a 3' overhang of 10 nt per target fragment. 2 μL of the fragments including the target sequences and the resistance gene units and 2 μL of the target fragments are taken and mixed, and then directly transformed into the *Escherichia Coli* followed by adding an LB liquid medium containing 50 g/mL kanamycin for culturing to obtain 10 recombined plasmids pNEW(Kan$^r$) (i.e., pNEW(Kan$^r$) 1-6, pNEW (Kan$^r$) 7-12, pNEW(Kan$^r$) 13-18, pNEW(Kan$^r$) 19-24, pNEW(Kan$^r$) 25-30, pNEW(Kan$^r$) 31-36, pNEW(Kan$^r$)

Figure 9:
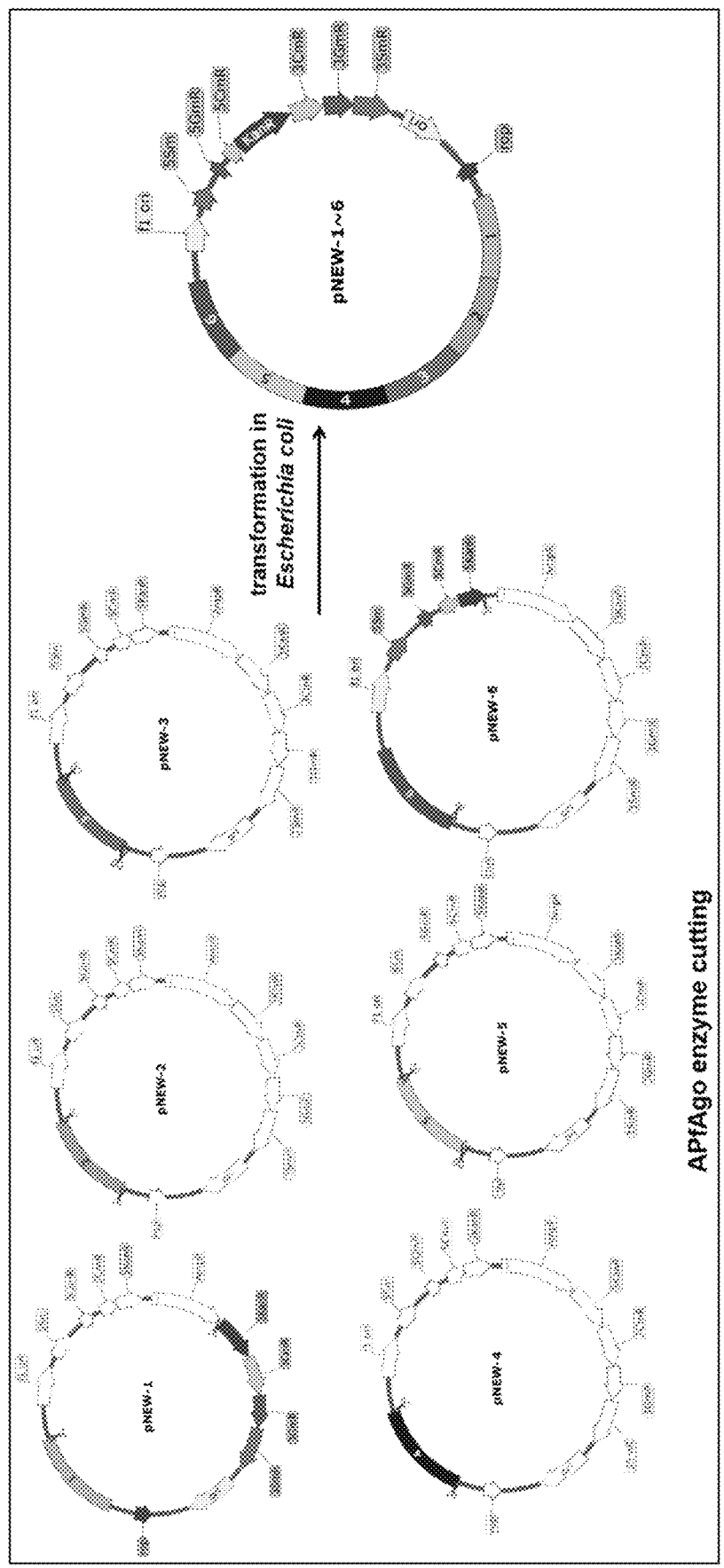
FIG. 9 illustrates a schematic diagram of a first step (first SLIC and Kan resistance gene reconstruction) for assembling the large fragment DNA (assembling and reconstructing 6 plasmids at a time) based on the strategy of Argonaute, SLIC, and antibiotic resistance gene reconstruction according to the embodiment of the disclosure.
Figure 10:
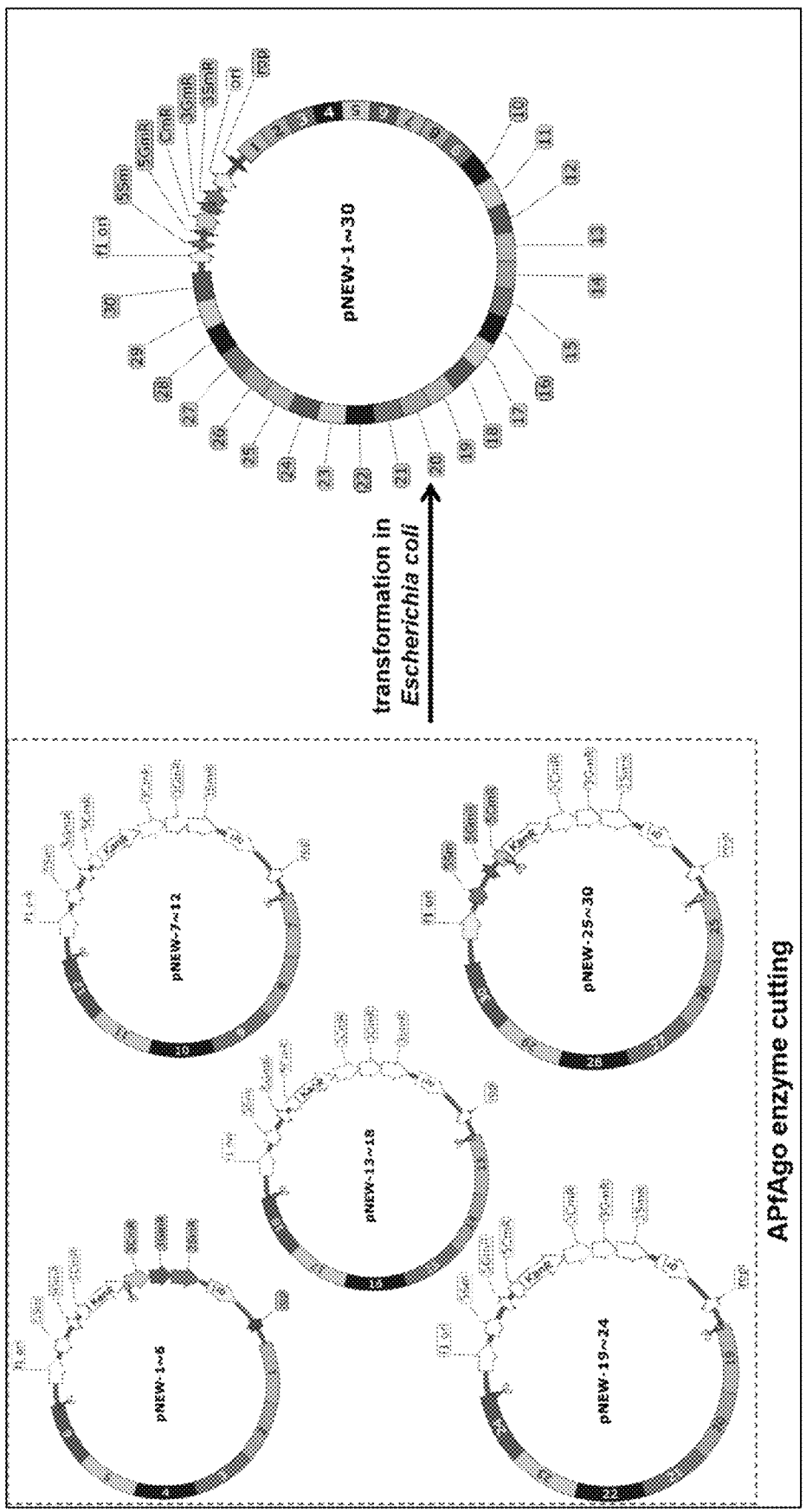
FIG. 10 illustrates a schematic diagram of a second step (second SLIC and Chl resistance gene reconstruction) for assembling the large fragment DNA (assembling and reconstructing 6 plasmids at a time) based on the strategy of Argonaute, SLIC, and antibiotic resistance gene reconstruction according to the embodiment of the disclosure.
Figure 11:
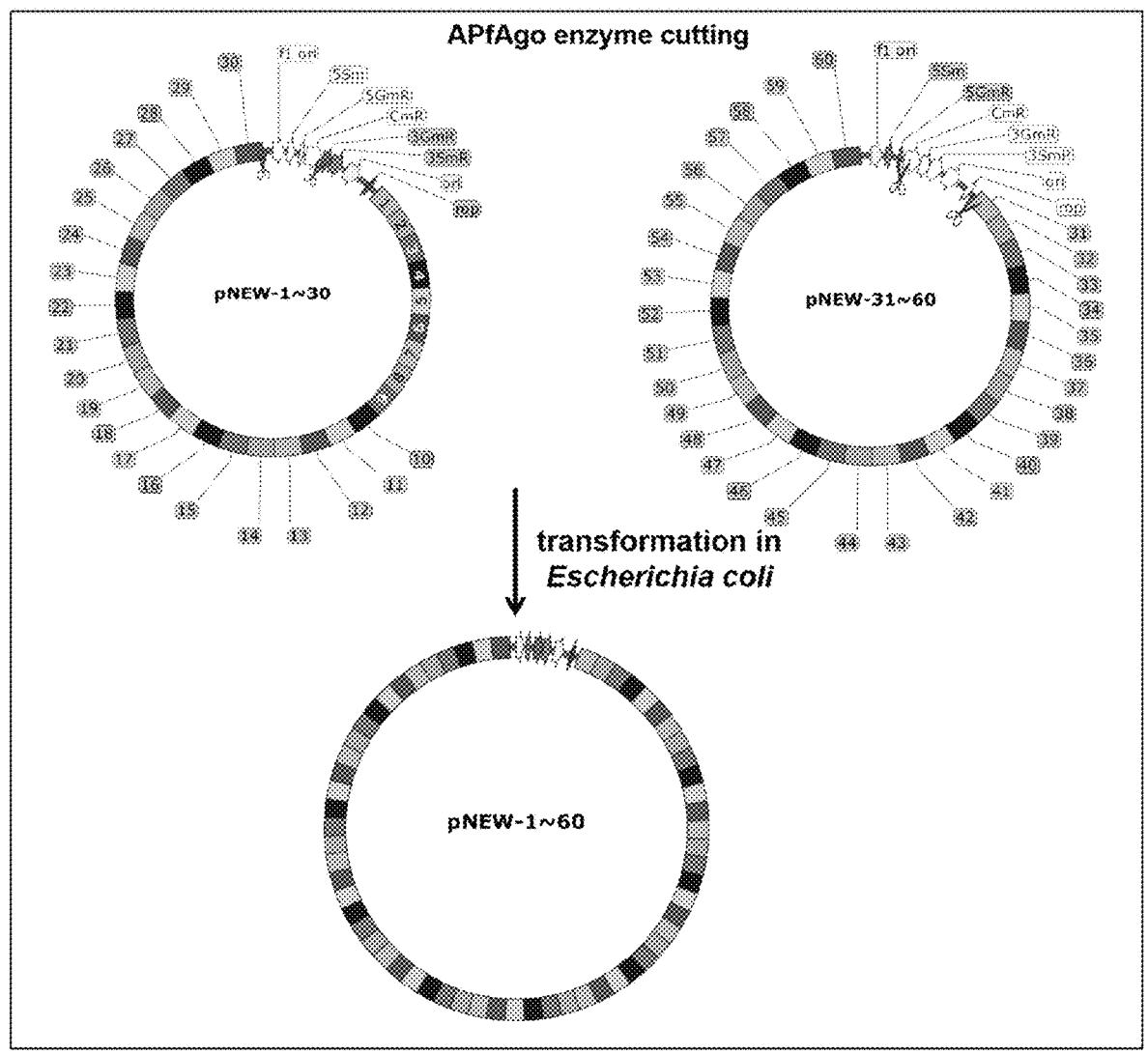
FIG. 11 illustrates a schematic diagram of a third step (Gen resistance gene reconstruction) for assembling the large fragment DNA (assembling and reconstructing 6 plasmids at a time) based on the strategy of Argonaute, SLIC, and antibiotic resistance gene reconstruction according to the embodiment of the disclosure.

37-42, pNEW(Kan$^r$) 43-48, pNEW(Kan$^r$) 49-54, pNEW(Kan$^r$) 55-60), and a target DNA fragment size of each recombined plasmid pNEW(Kan$^r$) is about 3 kb. The 10 recombined plasmids pNEW(Kan$^r$) are divided into 2 groups, with 5 recombined plasmids pNEW(Kan$^r$) per group, and reconstructed with chloramphenicol resistance genes and SLIC to obtain 2 recombined plasmids pNEW (Chl$^r$) (i.e., pNEW(Chl$^r$) 1-30 and pNEW(Chl$^r$) 31-60), with a target DNA fragment size of each recombined plasmid pNEW(Chl$^r$) about 15 kb. The 2 recombined plasmids pNEW(Chl$^r$) are cut and reconstructed with gentamicin resistance gene to obtain a recombined plasmid pNEW (Gen$^r$) (i.e., pNEW(Gen$^r$) 1-60) to obtain a 30 kb target DNA fragment. The assembly process is shown in FIG. 9-FIG. 11.

Since the starting plasmid is sequenced and verified to be correct, the disclosure assembles large fragment by plasmid reconstruction starting from a plasmid sequenced to be correct. The entire process does not involve PCR but only enzyme digestion, which eliminates the possibility of mutations introduced by PCR. Therefore, the recombinants selected through a positive genetic factor of antibiotic resistance genes are correct, i.e., the reconstructed large fragment do not need to be sequenced again, saving time and costs.

In summary, the disclosure divides the large fragment DNA that needs to be assembled into several small DNA fragments of 450-500 bp, and then loads the small DNA fragments into the antibiotic resistance gene reconstructed vector pNEW(Amp$^r$) plasmid, with 10 bp of homologous sequences at ends of adjacent small DNA fragments for SLIC. By utilizing the SLIC and the resistance gene reconstruction, the assembly of large fragment DNA can be achieved, and the number of times that resistance genes are reconstructed can be determined based on a length of the target DNA fragment. Moreover, the disclosure uses the programmable nuclease Argonaute with high enzyme cutting activity on plasmid DNA, to linearize the target plasmid. After cutting, sticky ends of the target fragments with homologous arms can anneal to form nicked circular DNA molecules, which are then repaired by the in vivo repair mechanism of the *Escherichia coli* to obtain the recombinant plasmid. This makes the method of the disclosure simple and efficient.

The efficient and low-cost large fragment DNA assembly technologies developed in the disclosure can provide a strong supplement for the development of synthetic biology underlying biotechnological tool kits, offering new ideas for the development of large fragment DNA synthesis and assembly technologies in the market, and has strong application value.

The above is a specific embodiment of the disclosure and cannot be used to limit the scope of the rights of the disclosure. It should be pointed out that for those skilled in the art, any modifications, equivalent substitutions, and improvements made within the spirit and principles of the disclosure should be included in the scope of protection of the disclosure.

SEQUENCE LISTING

```
Sequence total quantity: 15
SEQ ID NO: 1            moltype = AA   length = 770
FEATURE                 Location/Qualifiers
source                  1..770
                        mol_type = protein
                        organism = synthetic construct
SEQUENCE: 1
MKAIVVINLV KINKKIIPDK IYVYRLFNDP EEELQKEGYS IYRLAYENVG IVIDPENLII   60
ATTKELEYEG EFIPEGEISF SELRNDYQSK LVLRLLKENG IGEYELSKLL RKFRKPKTFG  120
DYKVIPSVEM SVIKHDEDFY LVIHIIHQIQ SMKTLWELVN KDPKELEEFL MTHKENLMLK  180
DIASPLKTVY KPCFEEYTKK PKLDHNQEIV KYWYNYHIER YWNTPEAKLE FYRKFGQVDL  240
KQPAILAKFA SKIKKNKNYK IYLLPQLVVP TYNAEQLESD VAKEILEYTK LMPEERKELL  300
ENILAEVDSD IIDKSLSEIE VEKIAQELEN KIRVRDDKGN SVPISQLNVQ KSQLLLWTNY  360
SRKYPVILPY EVPEKFRKIR EIPMFIILDS GLLADIQNFA TNEFRELVKS MYYSLAKKYN  420
SLAKKARSTN EIGLPFLDFR GKEKVITEDL NSDKGIIEVV EQVSSFMKGK ELGLAFIAAR  480
NKLSSEKFEE IKRRLFNLNV ISQVVNEDTL KNKRDKYDRN RLDLFVRHNL LFQVLSKLGV  540
KYYVLDYRFN YDYIIGIDVA PMKRSEGYIG GSAVMFDSQG YIRKIVPIKI GEQRGESVDM  600
NEFFKEMVDK FKEFNIGYDN KKILLLRDGR ITNNEEEGLK YISEMFDIEV VTMDVIKNHP  660
VRAFANMKMY FNLGGAIYLI PHKLKQAKGT PIPIKLAKKR IIKNGKVEKQ SITRQDVLDI  720
FILTRLNYGS ISADMRLPAP VHYAHKFANA IRNEWKIKEE FLAEGFLYFV             770

SEQ ID NO: 2            moltype = DNA   length = 2313
FEATURE                 Location/Qualifiers
source                  1..2313
                        mol_type = other DNA
                        organism = synthetic construct
SEQUENCE: 2
agcatgaaag ccattgtggt gattaacctg gtgaaaatca acaaaaaaat catcccggat   60
aaaatctacg tgtaccgcct gtttaatgat ccggaagaag aactgcagaa agaaggctat  120
agcatttatc gtctggccta tgaaaatgtg ggcattgtta tcgatccgga aaatctgatt  180
attgccacca ccaaagaact ggaatatgaa ggtgaattta ttccggaagg cgaaatcagc  240
tttagcgaac tgcgtaatga ttatcagagc aaactggttc tgcgtctgct gaaagaaaat  300
ggtattggtg aatatgaact gtccaaactg ctgcgcaaat ttcgtaaacc gaaaaccttt  360
ggcgattaca aagttattcc gagcgttgaa atgagcgtga tcaaacacga tgaagatttc  420
tatctggtga tccatatcat ccatcagatc cagagcatga aaaccctgtg ggaactggtt  480
aataaagatc cgaaagagct ggaagaattt ctgatgaccc ataaagaaaa cctgatgctg  540
aaagatattg ccagtccgct gaaaaccgtg tataaaccgt gttttgaaga atataccaaa  600
aaaccgaaac tggaccacaa ccaagagatc gtgaaatatt ggtataacta tcacatcgag  660
cgctattgga atacaccgga agcaaaactg gaattctatc gcaaatttgg tcaggttgat  720
ctgaaacagc ctgcaattct ggcaaaattt gcaagcaaaa ttaaaaaaaa taaaaactac  780
aaaatctatc tgctgccgca gctggttgtt ccgacctata atgcagaaca gctggaaagt  840
```

-continued

```
gatgtggcca aagaaattct ggaatataca aaactgatgc ctgaggaacg taaagagctg    900
ctggaaaata ttctggcaga agtggatagc gatatcatcg ataaaagcct gagcgaaatc    960
gaggttgaaa aaattgcaca agaactggaa aacaaaatcc gcgtgcgtga tgataaaggt   1020
aatagcgttc cgattagcca gctgaatgtt cagaaaagcc agctgctgct gtggaccaat   1080
tattcacgta aatatccggt tatcctgccg tatgaagtgc tggaaaaatt tcgcaaaatt   1140
cgtgaaatcc cgatgttcat tattctggat agcggtctgc tggcagatat tcagaacttt   1200
gcaaccaatg aatttcgcga gctggtcaaa agcatgtatt atagcctggc caaaaaatac   1260
aactccctgg caaaaaaagc acgcagcacc aatgaaattg gtctgccgtt tctggatttt   1320
cgcggtaaag aaaaagtgat caccgaagat ctgaataagc ataaaggcat tattgaagtt   1380
gttgaacagg tgagcagctt tatgaaaggt aaagaactgg gtctggcatt tattgcagca   1440
cgtaataaac tgagcagcga gaaatttgaa gaaatcaaac gccgtctgtt taacctgaat   1500
gttattagcc aggtggtgaa tgaagatacc ctgaaaaaca aacgcgataa atatgatcgt   1560
aatcgcctgg acctgtttgt tcgtcataat ctgctgttcc aggttctgag taaactgggt   1620
gttaaatact atgtgctgga ctatcgcttc aactacgatt atatcattgg cattgatgtg   1680
gcaccgatga aacgtagcga aggttatatt ggtggtagcg cagttatgtt tgatagccag   1740
ggttatattc gtaaaatcgt gccgattaaa atcggtgaaa agcgtggtga aagcgttgat   1800
atgaacgaat ttttcaaaga aatggtggac aaattcaaag agttcaacat cgggtatgat   1860
aacaaaaaaa tcctgctgct gcgtgatggt cgcattacca ataatgaaga agaaggcctg   1920
aaatatatca gcgagatgtt cgatattgaa gtggttacca tggatgtgat caaaaaccat   1980
ccggttcgtg catttgcaaa catgaaaatg tattttaacc tgggtggtgc catttatctg   2040
attccgcata aactgaaaca ggcaaaaggc accccgattc cgattaaact ggcgaaaaaa   2100
cgcattatca aaaacggcaa agtggaaaaa cagagcattc cccgtcagga tgttctgcat   2160
atctttattc tgacccgtct gaattatggt agcattagcg cagatatgcg tctgcctgca   2220
ccggttcatt atgcacataa atttgccaat gccattcgca acgagtggaa aatcaaagaa   2280
gaattcctgg ccgaaggctt tctgtatttt gtt                                2313

SEQ ID NO: 3                   moltype = DNA  length = 306
FEATURE                        Location/Qualifiers
source                         1..306
                               mol_type = other DNA
                               organism = synthetic construct
SEQUENCE: 3
atgcagttta aggtttacac ctataaaaga gagagccgtt atcgtctgtt tgtggatgta     60
cagagtgata ttattgacac gcccgggcga cggatggtga tccccctggc cagtgcacgt    120
ctgctgtcag ataaagtctc ccgtgaactt tacccgtctg tgcatatcgg ggatgaaagc    180
tggcgcatga tgaccaccga tatggccagt gtgccggtct ccgttatcgg ggaagaagtg    240
gctgatctca gccaccgcga aaatgacatc aaaaacgcca ttaacctgat gttctgggga    300
atataa                                                               306

SEQ ID NO: 4                   moltype = DNA  length = 25
FEATURE                        Location/Qualifiers
source                         1..25
                               mol_type = other DNA
                               organism = synthetic construct
SEQUENCE: 4
tagtatgtat tatatttctc cgaaa                                           25

SEQ ID NO: 5                   moltype = DNA  length = 25
FEATURE                        Location/Qualifiers
source                         1..25
                               mol_type = other DNA
                               organism = synthetic construct
SEQUENCE: 5
atcatacata atataaagag gcttt                                           25

SEQ ID NO: 6                   moltype = AA   length = 8
FEATURE                        Location/Qualifiers
source                         1..8
                               mol_type = protein
                               organism = synthetic construct
SEQUENCE: 6
SMYYISPK                                                               8

SEQ ID NO: 7                   moltype = DNA  length = 25
FEATURE                        Location/Qualifiers
source                         1..25
                               mol_type = other DNA
                               organism = synthetic construct
SEQUENCE: 7
gcagaatagg aataacatcc tcgac                                           25

SEQ ID NO: 8                   moltype = DNA  length = 25
FEATURE                        Location/Qualifiers
source                         1..25
                               mol_type = other DNA
                               organism = synthetic construct
SEQUENCE: 8
cgtcttatcc ttattgtagg agctg                                           25
```

```
SEQ ID NO: 9              moltype = AA   length = 8
FEATURE                   Location/Qualifiers
source                    1..8
                          mol_type = protein
                          organism = synthetic construct
SEQUENCE: 9
QNRNNILD                                                                    8

SEQ ID NO: 10             moltype = DNA  length = 25
FEATURE                   Location/Qualifiers
source                    1..25
                          mol_type = other DNA
                          organism = synthetic construct
SEQUENCE: 10
gcttaacatt aaaaaaagca tgaaa                                                25

SEQ ID NO: 11             moltype = DNA  length = 25
FEATURE                   Location/Qualifiers
source                    1..25
                          mol_type = other DNA
                          organism = synthetic construct
SEQUENCE: 11
cgaattgtaa ttttttcgt acttt                                                 25

SEQ ID NO: 12             moltype = AA   length = 8
FEATURE                   Location/Qualifiers
source                    1..8
                          mol_type = protein
                          organism = synthetic construct
SEQUENCE: 12
LNIKKSMK                                                                    8

SEQ ID NO: 13             moltype = DNA  length = 25
FEATURE                   Location/Qualifiers
source                    1..25
                          mol_type = other DNA
                          organism = synthetic construct
SEQUENCE: 13
gaagcgcgtc aatgcacata tgacc                                                25

SEQ ID NO: 14             moltype = DNA  length = 25
FEATURE                   Location/Qualifiers
source                    1..25
                          mol_type = other DNA
                          organism = synthetic construct
SEQUENCE: 14
cttcgcgcag ttacgtgtat actgg                                                25

SEQ ID NO: 15             moltype = AA   length = 8
FEATURE                   Location/Qualifiers
source                    1..8
                          mol_type = protein
                          organism = synthetic construct
SEQUENCE: 15
KRVNAHMT                                                                    8
```

What is claimed is:

1. A synthesis and assembly method for fragment deoxyribonucleic acid (DNA) based on a programmable nuclease Argonaute, comprising:
   S1, constructing plasmids as antibiotic resistance gene vectors, wherein each plasmid comprises a filler fragment and resistance gene fragments, with m base pairs (bp) of a homologous sequence between the resistance gene fragments;
   S2, excising the filler fragment from each plasmid by using the programmable nuclease Argonaute and guide DNA (gDNA) to obtain linear vectors each with a 3' overhang of m nucleotides (nt);
   S3, dividing a target DNA into n small DNA fragments with 450-500 bp, and synthesizing the small DNA fragments and introducing m nt of sequences which are complementary to homologous sequences of the linear vectors to the small DNA fragments to obtain synthesized small DNA fragments;
   S4, mixing and transforming the linear vectors obtained from the step S2 and the synthesized small DNA fragments obtained from the step S3 in competent cells of *Escherichia coli* to obtain recombined plasmids 1, 2, 3 to n; and
   S5, assembling the recombined plasmids 1, 2, 3 to n;
   wherein the amino acid sequence of the programmable nuclease Argonaute is shown in SEQ ID NO: 1.

2. The synthesis and assembly method for the fragment DNA as claimed in claim 1, wherein a resistance gene in each plasmid is one or more selected from the group consisting of a Kanamycin resistance gene (Kan$^r$), a Chloramphenicol resistance gene (Chl$^r$), a Gentamicin resistance gene (Gen$^r$) and a Spectinomycin resistance gene (Spe$^r$).

3. The synthesis and assembly method for the fragment DNA as claimed in claim 2, wherein the resistance gene comprises the Kan$^r$, the Chl$^r$, the Gen$^r$ and the Spe$^r$, and there are 10 bp of each homologous sequence between the resistance gene fragments 5Kana/3Kana, 5Chl/3Chl, 5Gen/3Gen, and 5Spe/3Spe.

4. The synthesis and assembly method for the fragment DNA as claimed in claim 1, wherein the filler fragment is ccdb lethal gene.

5. The synthesis and assembly method for the fragment DNA as claimed in claim 1, wherein the programmable nuclease Argonaute is capable of effectively cleaving double-stranded linear DNA and plasmid DNA under magnesium ion ($Mg^{2+}$) conditions, and cleaving double-stranded DNA with a guanine and cytosine (GC) content greater than or equal to 50%.

6. The synthesis and assembly method for the fragment DNA as claimed in claim 1, wherein the step S2 specifically comprises:
designing the gDNA with 16-18 nt in response to the homologous sequences and performing 5' phosphorylation treatment on the gDNA with 16-18 nt to obtain 5'-P gDNA, incubating the 5'-P gDNA and the programmable nuclease Argonaute, and then mixing the 5'-P gDNA and the programmable nuclease Argonaute with the plasmids for reaction, after the reaction, recovering the linear vectors each with the 3' overhang of m nt by using agarose gel electrophoresis.

7. The synthesis and assembly method for the fragment DNA as claimed in claim 1, wherein the synthesizing the small DNA fragments in the step S3 comprises:
designing oligonucleotide primer pairs which are overlapping in a length of 17-20 nt, and placing the oligonucleotide primer pairs and a buffer in a reaction tube for annealing followed by synthesizing the DNA fragments; wherein a length of each oligonucleotide primer is in a range of 50-59 nt, and 5' ends of the first and last oligonucleotide primers are introduced with the m nt of the sequences which are complementary to the homologous sequences of the linear vectors.

8. The synthesis and assembly method for the fragment DNA as claimed in claim 7, wherein procedures of the annealing comprise: 94 degrees Celsius (° C.) for 5 minutes (min), 94° C. to 37° C. slope 20 min, and 37° C. for 7 min.

9. The synthesis and assembly method for the fragment DNA as claimed in claim 1, wherein the step S5 specifically comprises:
dividing the recombined plasmids 1, 2, 3 to n into x groups with 2-6 recombined plasmids per group, taking and cutting the first and last recombined plasmids from each group with the programmable nuclease Argonaute to obtain fragments comprising target sequences and resistance gene units, cutting middle recombined plasmids from each group with the programmable nuclease Argonaute to obtain target fragments each with only a 3' overhang of m nt, mixing and transferring the fragments comprising the target sequences and the resistance gene units with the target fragments to competent cells of *Escherichia coli* to obtain x new recombined plasmids, and repeating above steps until the small DNA fragments are assembled to the target DNA.

* * * * *